United States Patent [19]

Abacherli

[11] Patent Number: 4,564,696
[45] Date of Patent: * Jan. 14, 1986

[54] PROCESS FOR THE PRODUCTION OF 4-ALKOXYACETOACETIC ACID ESTERS

[75] Inventor: Claudio Abacherli, Visp, Switzerland

[73] Assignee: Lonza Ltd., Gampel, Switzerland

[*] Notice: The portion of the term of this patent subsequent to Sep. 10, 2002 has been disclaimed.

[21] Appl. No.: 423,569

[22] Filed: Sep. 27, 1982

[30] Foreign Application Priority Data

Oct. 1, 1981 [CH] Switzerland .......................... 6320/81

[51] Int. Cl.$^4$ .............................................. C07C 69/76
[52] U.S. Cl. ...................................... 560/53; 560/174; 560/178
[58] Field of Search .......................... 560/178, 13, 174

[56] References Cited

FOREIGN PATENT DOCUMENTS 562191  4/1975  Switzerland .......................... 560/653

OTHER PUBLICATIONS

J. Amer. Chem. Soc., 68 (1946), 2392.
Chem. Abstr., 43, (1949) 2625e.
J. Amer. Chem. Soc., 70, (1948), p. 500.
Bull. Soc. Chim. France, 4th Series, 29 (1921), pp. 402–406.
T. Kato, J. Chem. Soc., Perkin I, 529, (1979).

*Primary Examiner*—Paul J. Killos
*Attorney, Agent, or Firm*—Fisher, Christen & Sabol

[57] ABSTRACT

Process for the production of 4-alkoxyacetoacetic acid esters from 4-chloro or 4-bromoacetoacetic acid esters. 4-chloro or 4-bromoacetoacetic acid ester is reacted with more than one equivalent of an alkali alcoholate in an aprotic solvent effectively at a temperature of 50° to 100° C.

14 Claims, No Drawings

PROCESS FOR THE PRODUCTION OF 4-ALKOXYACETOACETIC ACID ESTERS

BACKGROUND OF THIS INVENTION

1. Field of this Invention

This invention relates to a process for the production of 4-alkoxyacetoacetic esters.

2. Prior Art 4-ethoxyacetoacetic ester has been produced by reaction of bromoacetic ester and ethoxyacetic ester with zinc [J. Amer. Chem. Soc., 68, (1946), 2392] or by reaction of ethoxyacetic ester with acetic ester in the presence of sodium [Chem. Abstr., 43, (1949), 2625e]. 4-methoxyacetoacetic ester has been produced by condensation of methoxyacetylchloride with malonic acid ethyl tert.-butyl ester with subsequent saponification and decarboxylation [J. Amer. Chem. Soc., 70, (1948), p. 500]. The yields obtained according to these processes are in the neighborhood of 11, 21 or 40 percent, respectively.

Experiments designed to produce 4-ethoxyacetoacetic ester from 4-chloroacetoacetic ester with equimolar quantities of Na-alcoholates in alcohol failed. Instead of the anticipated 4-ethoxyacetoacetic ester, succinyl succinic acid diethyl ester was obtained [Bull. Soc. Chim. France, 4th series, 29, (1921), pp. 402–406].

Swiss Pat. No. 562,191 teaches the successful production of 4-alkoxyacetoacetic esters from 4-haloacetoacetic esters with alkali alcoholates whenever the operation is conducted in a mixture of an alcohol and an aprotic solvent with high dielectricity constant, preferably dimethyl sulfoxide, at a temperature of 15° to 30° C. The disadvantages of such process are that reaction times of 24 to 72 hours are required and that the reaction must be carried out in a large quantity of the solvent mixture.

T. Kato, J. Chem. Soc., Perkin I, 529, (1979), teaches the production of 4-ethoxyacetoacetic ester from 4-bromoacetoacetic ester. According to this paper, one equivalent of 4-bromoacetoacetic ester is reacted with 2.2 equivalents of sodium ethylate. Large quantities of ethanol serve as the solvent, but the yields of 47 percent are very modest.

BROAD DESCRIPTION OF THIS INVENTION

An object of this invention is to provide a process for the production of the hitherto difficulty accessible 4-alkoxyacetoacetic ester in high yields with a simple execution and a short reaction time. Another object of this invention is to provide a composition for use in said process. Other objects and advantages of this invention are set out herein or are obvious herefrom to one ordinarily skilled in the art.

The objects and advantages of this invention are achieved by the process and composition of this invention.

This invention involves a process for producing 4-alkoxyacetoacetic acid esters, which can be substituted in the 2-position with a substituent which does not react in a strongly basic medium. The process includes reacting a 4-chloroacetoacetic ester or a 4-bromoacetoacetic ester with an alkali alcoholate in a ratio of greater than 1.0 mole of alkali alcoholate per mole of 4-haloacetoacetic ester in an aprotic solvent, having a high donor number, effectively at a temperature of 50° to 100° C. Thus, one operates in the absence of alcohol.

As the aprotic solvent, a solvent with a high donor number is used. The solvents suitable for use in this invention can be defined by the donor number as physical constants. The donor number is defined as a physical solvent constant in V. Gutmann, Coordination Chemistry in Non-Aqueous Solutions, Springer-Verlag, Vienna-New York, (1968), as:

$$DN_{SbCl_5} = -\Delta H_{D.SbCl_5}$$

that is, the donor number $DN_{SbCl_5}$ is the negative reaction enthalpy of a donor solvent with antimony pentachloride, measured in 1,2-dichloroethane. Effectively solvents are used defined by a relatively high donor number, best above 11. Examples of useful aprotic solvents of such type are dimethyl sulfoxide, dimethyl formamide, formamide, N-methylformamide, N-methylpropionamide, dioxane and tetrahydrofuran. Preferably the aprotic solvent is acetonitrile or propionitrile. The quantity of aprotic solvent used is not critical; however, effectively the amount used should be at least large enough to allow effective stirring of the reaction mixture. When operating with the above-mentioned aprotic solvents, colorless to slightly yellow raw products are obtained.

The reaction temperature effectively is 50° to 100° C. and preferably is 60° to 80° C.

The alkali alcoholate is advantageously used in a quantity of 2.0 to 10 moles, preferably 2 to 3 moles, per mole of 4-haloacetoacetic ester. The alkali metal in the alkali alcoholates are effectively sodium and potassium. The alcohol component of the alkali alcoholate are those which are derived from straight-chained or branched aliphatic alcohols, effectively those which have 1 to 10 carbon atoms in the molecule. Such alcohols are, for example, methanol, ethanol, butanol, sec. butanol, propanol and isopropanol. Sodium methoxide is the preferred alkali alcoholate.

Of the 4-chloroacetoacetic esters or 4-bromoacetoacetic esters, especially the 4-chloro derivatives, are used. 4-chloroacetoacetic esters and 4-bromoacetoacetic esters substituted in the 2-position can also be used. Thus, the process of this invention produces a 4-alkoxyacetoacetic ester having the general formula:

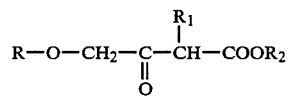

wherein R and $R_2$ are each alkyl and $R_1$ is H, alkyl, or substituted alkyl. The substituents R, $R_1$ and $R_2$ are subject to no numerical limitation of the included C atoms, but usually 1 to 12 carbon atoms are present. Any alkyl groups, whether straight-chained or branched, can be used. Substituted alkyl groups, for example, bearing methoxy, alkyl and/or aryl substituents, can be used. An essential characteristic of such substituents is that they do not react in a strongly basic medium. Examples of useful alkyl groups are methyl, ethyl, propyl, isopropyl, n-butyl, isobutyl, 2-butyl, 1-pentyl, 3-methyl-1-butyl, 2-pentyl, 1-hexyl, 2-methyl-1-pentyl, 3-methyl-1-pentyl, 4-methyl-1-pentyl, 2-ethyl-1-butyl, 2-hexyl, 2,3-dimethyl-1-butyl, 1-heptyl, 2,4-dimethyl-1-pentyl, 1-octyl, 2-octyl, 1-nonyl, 1-decyl, 1-undecyl, 1-dodecyl, 1-tetradecyl and 1-nonadecyl.

The process of this invention is particularly suited for the production of 4-alkoxyacetoacetic esters in which the 4-alkoxy group (R) and the alcohol group of the ester ($R_2$) have the same number of carbon atoms and are identical. When this process is used in the production of 4-alkoxyacetoacetic esters, in which the 4-alkoxy group is different from the alcohol group of the ester, then ester mixtures might be obtained upon transesterification.

The reaction according to this invention only requires a short reaction time. Effectively, the reaction is carried out over a 20 to 40 minute period. The 4-alkoxyacetoacetic ester is obtained from the reaction mixture available after the reaction, preferably in accordance with the following method:

While stirring, the reaction mixture is introduced into a batch of diluted acetic acid cooled in an ice bath, for example, prepared from glacial acetic acid and water. The acetic acid serves exclusively as a buffer component in order to avoid pH fluctuations which are too large. The volume of water should be effectively adjusted such that no precipitation of NaCl takes place. On the other hand, only so much water should be present that a phase separation will just take place.

Simultaneously with the dosing in of the reaction mixture, concentrated hydrochloric acid is added at such a rate that a pH value between 4.5 and 8 can be held at all the time and that at the end of the neutralization a pH of $6 \pm 1.0$ will be achieved.

The neutralized mixture is allowed to stand, the phases forming are separated, the aqueous phase with the aprotic solvent, preferably acetonitrile, is extracted and the two organic phases are united. From these organic phases, the 4-alkoxyacetoacetic ester is obtained by distillation.

As used herein and unless otherwise indicated, alkyl has 1 to 12 carbon atoms, and an example of aryl is benzyl.

This invention also includes a composition of (a) a 4-chloroacetoacetic ester or a 4-bromoacetoacetic ester, which can be substituted in the 2-position, (b) an aprotic solvent and (c) more than one equivalent of an alkali alcoholate based on the amount of the 4-chloroacetoacetic ester or 4-bromocacetoacetic ester.

By way of summary, the process of this invention produces a 4-alkoxyacetoacetic ester from 4-haloacetoacetic esters and alkali alcoholate in an aprotic solvent at a temperature of 50° to 100° C.

DETAILED DESCRIPTION OF THIS INVENTION

As used herein, all parts, ratios, percentages and proportions are on a weight basis unless otherwise stated herein or otherwise obvious herefrom to one ordinarily skilled in the art.

EXAMPLE 1

77.4 g of sodium methylate, 97 percent, was suspended in 100 g of acetonitrile at ambient temperature. To this well-stirred suspension, 101.9 g of 97.5 percent 4-chloroacetoacetic acid methyl ester was added by drops through a drip funnel with a drop counter over a 5 to 6 minute period under $N_2$ atmosphere. The temperature rose and was kept by means of cooling at 68° to 70° C. As soon as the heat development slackened, the cooling water was turned off and the reaction mass was heated with 70° C. hot water. This pastelike, mustard-yellow reaction mixture continued to be stirred at 70° C. for 24 to 25 minutes and, with stirring, was then slowly introduced into a solution of 6 g of glacial acetic acid and 215 g of water cooled in an ice bath. At the same time, 37.4 percent hydrochloric acid was introduced drop by drop from a burette. At the same time, the pH was measured by means of a glass electrode and kept between 4.5 and 8 by adjusting the addition rate of the reaction mixture and/or HCl. At the end of the neutralization, the pH was $6.1 \pm 0.1$. For the neutralization, 56.4 ml of hydrochloric acid were used (37.4 percent) and the temperature was kept at 30° to 35° C. The neutralized mixture was put into a separating funnel. After standing a short time, the resultant layers were separated. The aqueous layer was extracted once with 200 ml and then twice each time with 100 ml of acetonitrile. The united organic phases were concentrated in a rotary evaporator at 30° to 35° C. and $\simeq 20$ torr up to a constant weight. The solvent evaporated off was regenerated and used with the next batch. The raw product was distilled at 0.5 to 1.5 torr/90° C. 4-methoxyacetoacetic acid methyl ester was obtained in a yield of 91.7 percent, based on the amount of chloroester used. The purity of the product was 98.8 percent.

EXAMPLE 2

Using the method described in Example 1, 108.6 g of 4-chloroacetoacetic acid ethyl ester in 143 g of acetonitrile was reacted with 103.6 g of sodium ethylate. 4-ethoxyacetoacetic acid ethyl ester was obtained in a yield of 90.4 percent, related to the amount of 4-chloroacetoacetic acid ethyl ester used. The purity of the product was 98.5 percent.

EXAMPLE 3

Using the method described in Example 1, 101.9 g of 4-chloroacetoacetic acid methyl ester in 180 ml of acetonitrile was reacted with 84.6 g of sodium methylate at 60° C. The product yield was 88.0 percent and the product content was 98.9 percent.

EXAMPLE 4

Using the method described in Example 1, however, at 80° C., the product yield was 83.9 percent, and the product purity was 98.9 percent.

EXAMPLE 5

The method described in Example 1 was used except that 117 g of propionitrile was used as the solvent. The product yield was 90.3 percent and the product content was 99.1 percent.

EXAMPLE 6

The method described in Example 1 was used, except that 116 g of isobutyronitrile was used as the solvent. The product yield was 78.7 percent, and the product purity was 97.6 percent.

EXAMPLE 7

The method described in Example 1 was used, except that 101.9 g of 4-chloroacetoacetic acid methyl ester in 150 ml of tetrahydrofuran was reacted with 86.4 g of sodium methylate. The product yield was 83 percent and the product purity was 99.1 percent.

EXAMPLE 8

The method described in Example 1 was used, except that 130.0 g of 4-chloroacetoacetic acid butyl ester was reacted with 147.4 of sodium butylate. The product yield was 88.9 percent and the product purity was 97.8 percent.

What is claimed is:

1. Process for the production of a 4-alkoxyacetoacetic acid ester from a 4-chloroacetoacetic ester or a 4-bromoacetoacetic ester consisting of reacting a 4-chloroacetoacetic ester or a 4-bromoacetoacetic ester with more than one equivalent of an alkali alcoholate in at least one aprotic solvent at a temperature of 50° to 100° C., whereby the 4-alkoxyacetoacetic acid ester results, the 4-alkoxyacetoacetic acid ester having the formula:

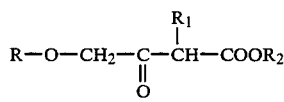

wherein R and $R_2$ are each alkyl, and $R_1$ is H, alkyl or substituted alkyl.

2. Process as claimed in claim 1 wherein the aprotic solvent is acetonitrile or propionitrile.

3. Process as claimed in claim 1 wherein at least 2.0 moles of the alkali alcoholate are used per mole of the 4-chloroacetoacetic ester or 4-bromoacetoacetic ester.

4. Process as claimed in claim 1 wherein the reaction is operated at a temperature of 60° to 80° C.

5. Process as claimed in claim 1 wherein $R_1$ is alkyl substituted with methoxy or aryl.

6. Process as claimed in claim 1 wherein $R_1$ is an alkyl group, having 1 to 12 carbon atoms, substituted with methoxy, benzyl or naphthyl.

7. Process as claimed in claim 1 wherein 2 to 10 moles of the alkali alcoholate are used per mole of the 4-chloroacetoacetic ester or 4-bromoacetoacetic ester.

8. Process as claimed in claim 1 wherein R is an alkyl group having 1 to 12 carbon atoms, $R_1$ is an alkyl group having 1 to 12 carbon atoms and $R_3$ is an alkyl group having 1 to 12 carbon atoms.

9. Process as claimed in claim 1 wherein the alkali metal in the alkali alcoholate is sodium or potassium and the alcohol component of the alkali alcoholate is an aliphatic alcohol having 1 to 10 carbon atoms.

10. Process as claimed in claim 1 wherein the aprotic solvent has a relative donor number which is above 11.

11. Process as claimed in claim 1 wherein the reaction is carried out over a time period of 20 to 40 minutes.

12. Process as claimed in claim 1 wherein one aprotic solvent is present.

13. Process for the production of a 4-alkoxyacetoacetic acid ester from a 4-chloroacetoacetic ester or a 4-bromoacetoacetic ester consisting of (a) reacting a 4-chloroacetoacetic ester or a 4-bromoacetoacetic ester with more than one equivalent of at least one alkali alcoholate in at least one aprotic solvent at a temperature of 50° to 100° C., whereby the 4-alkoxyacetoacetic acid ester results, the 4-alkoxyacetoacetic acid ester has the formula:

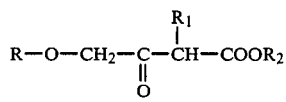

wherein R and $R_2$ are each alkyl, and $R_1$ is H, alkyl or substituted alkyl, and (b) separating the 4-alkoxyacetoacetic acid ester from reaction mixture (a).

14. Process as claimed in claim 13 wherein separation (b) comprises:

(i) introducing separately and simultaneously reaction mixture (a) and hydrochloric acid into a solution of acetic acid and water, solution (i) being cooled, the amount of water present in solution (i) being sufficient to prevent precipitation of NaCl, but not so large that a phase separation is prevented, sufficient hydrochloric acid being added to maintain solution (i) at a pH between 4.5 and 8;

(ii) allowing the neutralized solution (i) to stand until phases are formed;

(iii) separating the aqueous phase and combining the remaining two organic phases; and (iv) removing the 4-alkoxyacetoacetic acid ester from the organic phases by distillation.

* * * * *